United States Patent
Dwyer et al.

(10) Patent No.: US 10,960,165 B2
(45) Date of Patent: Mar. 30, 2021

(54) MOISTURE REMOVAL AND CONDENSATION AND HUMIDITY MANAGEMENT APPARATUS FOR A BREATHING CIRCUIT

(71) Applicant: TELEFLEX MEDICAL INCORPORATED, Morrisville, NC (US)

(72) Inventors: Daniel P. Dwyer, Cary, NC (US); Christopher S. Jackson, Knightdale, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 177 days.

(21) Appl. No.: 16/029,932

(22) Filed: Jul. 9, 2018

(65) Prior Publication Data

US 2019/0009047 A1  Jan. 10, 2019

Related U.S. Application Data

(60) Provisional application No. 62/530,631, filed on Jul. 10, 2017.

(51) Int. Cl.
*A61M 16/08* (2006.01)
*A61M 16/10* (2006.01)

(52) U.S. Cl.
CPC .... *A61M 16/0808* (2013.01); *A61M 16/0883* (2014.02); *A61M 16/1095* (2014.02); *A61M 2205/3653* (2013.01)

(58) Field of Classification Search
CPC .......... A61M 16/0808; A61M 16/1095; A61M 16/0883; A61M 2205/3653; A61M 16/16;
(Continued)

(56) References Cited

U.S. PATENT DOCUMENTS 2,362,985 A   11/1944  Brown, Jr.
2,702,089 A    2/1955  Engelder
(Continued)

FOREIGN PATENT DOCUMENTS

EP   0533644 B1   12/1996
EP   0794809 B1    6/1999
(Continued)

OTHER PUBLICATIONS

Technical Note TN-157: Moisture Exchange Tubes for Humidity Control of Test Gases, Raesystems by Honeywell, Jul. 29, 2014.
(Continued)

*Primary Examiner* — Kendra D Carter
*Assistant Examiner* — Arielle Wolff
(74) *Attorney, Agent, or Firm* — BakerHostetler

(57) ABSTRACT

A moisture removal apparatus for a breathing circuit includes a breathing gas conduit for receiving a flow of breathing gas having a first humidity level. A dry gas conduit is provided adjacent to at least a portion of the breathing gas conduit for receiving a flow of dry gas having a second humidity level lower than the first humidity level. A heating element extends from an upstream end of the breathing gas conduit to a downstream end of the breathing gas conduit. The heating element provides heat to the flow of breathing gas such that the breathing gas at the downstream end is heated to a higher temperature than the breathing gas at the upstream end. A moisture transmission pathway enables transfer of moisture from the breathing gas to the dry gas based on the humidity differential.

19 Claims, 10 Drawing Sheets

(58) Field of Classification Search
CPC .. A61M 16/161; A61M 16/14; A61M 16/142; A61M 16/145; B01F 3/02
See application file for complete search history.

(56) References Cited

U.S. PATENT DOCUMENTS

| | | | |
|---|---|---|---|
| 3,735,558 A | 5/1973 | Skarstrom et al. | |
| 3,747,598 A | 7/1973 | Cowans | |
| 4,146,597 A | 3/1979 | Eckstein et al. | |
| 4,155,961 A | 5/1979 | Benthin | |
| 4,200,094 A | 4/1980 | Gedeon et al. | |
| 4,232,667 A | 11/1980 | Chalon et al. | |
| 4,318,398 A | 3/1982 | Oetjen et al. | |
| 4,355,636 A | 10/1982 | Oetjen et al. | |
| 4,381,267 A | 4/1983 | Jackson | |
| 4,637,384 A | 1/1987 | Schroeder | |
| 4,808,201 A | 2/1989 | Kertzman | |
| 4,897,359 A | 1/1990 | Oakley et al. | |
| 5,042,500 A | 8/1991 | Norlien et al. | |
| 5,062,145 A | 10/1991 | Zwaan | |
| 5,097,898 A | 3/1992 | Verkaart | |
| 5,392,770 A | 2/1995 | Clawson et al. | |
| 5,501,212 A | 3/1996 | Psaros | |
| 5,537,996 A | 7/1996 | McPhee | |
| 6,014,971 A | 1/2000 | Danisch et al. | |
| 6,213,120 B1 | 4/2001 | Block et al. | |
| 6,220,245 B1 | 4/2001 | Takabayashi et al. | |
| 6,394,084 B1 | 5/2002 | Nitta | |
| 6,516,536 B2 | 2/2003 | Ryden | |
| 6,523,538 B1 | 2/2003 | Wikefeldt | |
| 6,536,428 B1 | 3/2003 | Smith et al. | |
| 6,662,802 B2 | 12/2003 | Smith et al. | |
| 6,769,431 B2 | 8/2004 | Smith et al. | |
| 6,776,820 B2 | 8/2004 | Bikson et al. | |
| 6,953,354 B2 | 10/2005 | Edirisuriya et al. | |
| 7,097,690 B2 | 8/2006 | Usher et al. | |
| 7,559,324 B2 | 7/2009 | Smith et al. | |
| 7,588,029 B2 | 9/2009 | Smith et al. | |
| 7,802,569 B2 | 9/2010 | Yeates et al. | |
| 8,037,882 B2 | 10/2011 | Smith et al. | |
| 8,105,410 B2 | 1/2012 | Roth et al. | |
| 8,230,857 B2 | 7/2012 | Cewers | |
| 8,236,081 B2 | 8/2012 | Roth et al. | |
| 8,242,081 B2 | 8/2012 | Divita et al. | |
| 8,453,641 B2 | 6/2013 | Payton et al. | |
| 8,616,202 B2 | 12/2013 | Tatkov et al. | |
| 8,893,748 B2 | 11/2014 | Malas et al. | |
| 9,067,036 B2 | 6/2015 | Korneff et al. | |
| 9,827,393 B2 | 11/2017 | Smith et al. | |
| 2002/0129815 A1* | 9/2002 | McPhee | A61M 16/109 128/200.24 |
| 2004/0250815 A1 | 12/2004 | Scott et al. | |
| 2006/0021615 A1 | 2/2006 | Kertzman | |
| 2006/0162554 A1 | 7/2006 | Kelley | |
| 2007/0157929 A1 | 7/2007 | Radomski et al. | |
| 2007/0157931 A1 | 7/2007 | Parker | |
| 2008/0110458 A1 | 5/2008 | Srinivasan | |
| 2008/0229605 A1 | 9/2008 | Brown | |
| 2009/0088656 A1 | 4/2009 | Levitsky et al. | |
| 2009/0211579 A1 | 8/2009 | Smith et al. | |
| 2010/0218763 A1 | 9/2010 | Payton et al. | |
| 2010/0294280 A1 | 11/2010 | Kratzenstein | |
| 2011/0108031 A1 | 5/2011 | Korneff et al. | |
| 2011/0315140 A1 | 12/2011 | Shuman | |
| 2012/0174924 A1 | 7/2012 | Smith et al. | |
| 2013/0081626 A1 | 4/2013 | Pujol et al. | |
| 2013/0098360 A1 | 4/2013 | Hurmez | |
| 2013/0112201 A1 | 5/2013 | Graham et al. | |
| 2013/0263845 A1 | 10/2013 | Arcilla et al. | |
| 2013/0303977 A1 | 11/2013 | Spearman et al. | |
| 2013/0306075 A1 | 11/2013 | Payton et al. | |
| 2014/0158130 A1 | 6/2014 | Coleman et al. | |
| 2014/0261416 A1 | 9/2014 | Arcilla et al. | |
| 2014/0283829 A1 | 9/2014 | Miller | |
| 2014/0311487 A1 | 10/2014 | Buechi et al. | |
| 2015/0048530 A1 | 2/2015 | Cheung et al. | |
| 2015/0083121 A1 | 3/2015 | Isher et al. | |
| 2015/0101607 A1 | 4/2015 | Virr et al. | |
| 2015/0209528 A1 | 7/2015 | Lee et al. | |
| 2016/0022949 A1 | 1/2016 | Milne et al. | |
| 2016/0022953 A1 | 1/2016 | Richards | |
| 2016/0045702 A1* | 2/2016 | Milne | A61M 16/161 128/204.17 |
| 2016/0256659 A1 | 9/2016 | Poormand | |
| 2016/0279374 A1 | 9/2016 | Graham et al. | |
| 2016/0287832 A1 | 10/2016 | Cortez, Jr. et al. | |
| 2016/0303342 A1* | 10/2016 | Dwyer | A61M 16/0875 |
| 2016/0317778 A1 | 11/2016 | Payton et al. | |
| 2017/0000967 A1 | 1/2017 | Sims et al. | |
| 2020/0030565 A1* | 1/2020 | Hermez | A61M 16/0875 |

FOREIGN PATENT DOCUMENTS

| | | |
|---|---|---|
| EP | 2335760 A1 | 6/2011 |
| GB | 1 431 558 A | 4/1976 |
| GB | 2139110 A | 11/1984 |
| JP | 2000024111 A | 1/2000 |

OTHER PUBLICATIONS

International Preliminary Report on Patentability and Written Opinion issued in PCT/US2018/041200, dated Jan. 23, 2020.
International Search Report and Written Opinion issued in PCT/US2018/041200, dated Sep. 12, 2018.

* cited by examiner

MOISTURE REMOVAL AND CONDENSATION AND HUMIDITY MANAGEMENT APPARATUS FOR A BREATHING CIRCUIT

CROSS-REFERENCE TO RELATED APPLICATIONS

This application claims priority to U.S. Provisional Patent Application No. 62/530,631 filed Jul. 10, 2017, the content of which is incorporated herein by reference in its entirety.

FIELD OF THE DISCLOSURE

The present disclosure relates generally to a medical device. More particularly, the present disclosure is related to a moisture removal and condensation and humidity management apparatus for a breathing circuit.

BACKGROUND

A breathing circuit delivers medical gas to a patient under pressure in a prescribed volume and breathing rate. The medical gas is often humidified by a humidifier located at or near the ventilator or respirator. The optimum respiratory circuit delivers 100% RH medical gases to the patient while reducing the amount of humidity and subsequent condensate delivered back to the ventilator through the expiratory limb. Therefore, the humidified gas has to travel through all or most of the tubing and has time to cool. Cooling of the gas leads to rainout or condensation in the breathing tube and collection of water within the breathing circuit. It is known that excessive condensate entering a device, such as a ventilator or respirator, from the expiratory limb of a respiratory circuit can harm the device.

Several possible solutions to the problem of rainout have been developed. One such proposed solution is a heating wire provided along the length of the breathing tube. The wire heats the humidified gas traveling through the tubing to prevent the gas from cooling, thus preventing the problem of water condensing out of the gas traveling through the breathing circuit. The thermal output from such a heating wire is usually achieved by imposing an electrical current in the wire so that the generated heat is released to the flow of gas, such as by convection.

Conventional heating wires are typically straight and extend along the length of the breathing tube so that uniform heating of the gas can be achieved. Coiled heating wires which are spirally wound around the breathing tube along its length are also commonly used to achieve uniform heating of the gas. However, such breathing circuit configurations that have an even heating distribution across the circuit, or breathing circuit configurations that have a higher temperature at an upstream end, can lead to rain out and condensation accumulation in the ventilator.

Accordingly, it is desirable to provide an improved apparatus for removing or decreasing water vapor, moisture, and/or condensate in a breathing circuit. It is further desirable that the improved apparatus for removing water vapor, moisture and/or condensate from the breathing tube, eliminates or reduces rain out and condensate in the ventilator, thus protecting the device from damage. Further, there is a need to increase the capacity for moisture removal and condensation management in a breathing circuit.

SUMMARY OF THE DISCLOSURE

The foregoing needs are met, to a great extent, by the present disclosure, wherein a moisture removal and condensation and humidity management apparatus for a breathing circuit arranged between a patient and a ventilator is provided. The apparatus may include a breathing circuit tubing defining a breathing gas conduit and a dry gas conduit adjacent at least a portion of the breathing gas conduit, the breathing gas conduit configured to receive a flow of breathing gas having a first humidity level and the dry gas conduit configured to receive a flow of dry gas having a second humidity level lower than the first humidity level. The apparatus may also include at least one heated wire having a length extending from an upstream end of the breathing circuit tubing to a downstream end of the breathing circuit tubing, the at least one heated wire configured to provide heat to the flow of breathing gas such that the breathing gas at the downstream end is heated to a higher temperature than the breathing gas at the upstream end. The apparatus may further include a moisture transmission pathway between the breathing gas conduit and the dry gas conduit and configured to enable transfer of moisture from the breathing gas to the dry gas based on a humidity differential between the first and second humidity levels.

In one implementation of the disclosure, the moisture transmission pathway may comprise a permeable membrane that is permeable to water vapor but impermeable to liquid water.

In another implementation of the disclosure, the permeable membrane may form a portion of said breathing circuit tubing.

In another implementation of the disclosure, a portion of the heated wire may be provided within the breathing gas conduit.

In another implementation of the disclosure, the heated wire may comprise two wire strand portions connected to each other at the upstream end of the breathing circuit tubing proximate to the patient.

In another implementation of the disclosure, a portion of the heated wire may be folded back upon itself at the downstream end proximate to the ventilator.

In another implementation of the disclosure, the portion of the heated wire folded back upon itself is generally S-shaped.

In another implementation of the disclosure, a portion of the heated wire may be folded over itself at the downstream end of the breathing circuit tubing proximate to the ventilator such that six wire strand portions are formed at the downstream end.

In another implementation of the disclosure, the heated wire may comprise a variable resistance such that a downstream portion of the heated wire can be heated more than an upstream portion of the wire.

In another implementation of the disclosure, the heated wire may comprise coils having a pitch spacing between adjacent coils at an upstream portion of the wire that are different than a pitch spacing between adjacent coils at a downstream portion of the wire.

In another implementation of the disclosure, the breathing circuit tubing may be formed by an inner tube defining the breathing gas conduit, and the dry gas conduit may be formed by an outer tube surrounding the inner tube, the dry gas conduit being defined by an annular flow conduit defined between the inner tube and the outer tube.

In another implementation of the disclosure, the apparatus may further comprise a dividing wall formed between the inner tube and the outer tube in the annular space to divide the dry gas conduit into a delivery conduit for flow of dry gas from a first end of the breathing circuit tubing to a second end of the breathing circuit tubing, and a return conduit for flow of dry gas from the second end of the breathing circuit tubing to the first end of the breathing circuit tubing.

In another implementation of the disclosure, a portion of the heated wire may be provided within a lumen of the inner tube.

In another implementation of the disclosure, a portion of the heated wire may be embedded within a wall of the inner tube.

In another implementation of the disclosure, the breathing circuit tubing may be an expiratory limb of the breathing circuit such that the upstream end of the breathing circuit tubing is located proximate to a patient and the downstream end of the breathing circuit tubing is located proximate to the ventilator.

In another implementation of the disclosure, the apparatus may further comprise a feeding conduit extending through at least a portion of the dry gas conduit, the feeding conduit configured to supply the dry gas into the dry gas conduit.

In another implementation of the disclosure, the feeding conduit may include an inlet at the downstream end of the breathing circuit tubing.

In another implementation of the disclosure, the apparatus may further comprise a flow control element connected to the inlet of the feeding conduit and configured to control the flow of the dry gas into the feeding conduit.

In another implementation of the disclosure, the feeding conduit may include an outlet at the upstream end of the breathing circuit tubing.

In another implementation of the disclosure, a moisture removal and condensation and humidity management apparatus for a breathing circuit arranged between a patient and a ventilator is provided. The apparatus may comprise a breathing circuit tubing defining a breathing gas conduit configured to receive a flow of breathing gas; a moisture transmission pathway configured to enable transfer of moisture from the breathing gas conduit to ambient air; and at least one heated wire having a length extending from an upstream end of the breathing circuit tubing to a downstream end of the breathing circuit tubing, the at least one heated wire configured to provide heat to the flow of breathing gas such that the breathing gas at the downstream end is heated to a higher temperature than the breathing gas at the upstream end.

In another implementation of the disclosure, the moisture transmission pathway may comprise a permeable membrane that is permeable to water vapor but impermeable to liquid water.

In another implementation of the disclosure, the permeable membrane may form a portion of said breathing circuit tubing.

In another implementation of the disclosure, a portion of the heated wire may be provided within the breathing gas conduit.

In another implementation of the disclosure, the heated wire may comprise two wire strand portions connected to each other at the upstream end of the breathing circuit tubing proximate to the patient.

In another implementation of the disclosure, a portion of the heated wire may be folded back upon itself at the downstream end proximate to the ventilator.

In another implementation of the disclosure, the portion of the heated wire folded back upon itself is generally S-shaped.

In another implementation of the disclosure, a portion of the heated wire may be folded over itself at the downstream end of the breathing circuit tubing proximate to the ventilator such that six wire strand portions are formed at the downstream end.

In another implementation of the disclosure, the heated wire may comprise a variable resistance such that a downstream portion of the heated wire can be heated more than an upstream portion of the wire.

In another implementation of the disclosure, the heated wire may comprise coils having a pitch spacing between adjacent coils at an upstream portion of the wire that are different than a pitch spacing between adjacent coils at a downstream portion of the wire.

In another implementation of the disclosure, the breathing circuit tubing may be formed by a tube defining the breathing gas conduit.

In another implementation of the disclosure, a portion of the heated wire may be provided within a lumen of the tube.

In another implementation of the disclosure, a portion of the heated wire may be embedded within a wall of the tube.

In another implementation of the disclosure, the breathing circuit tubing may be an expiratory limb of the breathing circuit such that the upstream end of the breathing circuit tubing is located proximate to a patient and the downstream end of the breathing circuit tubing is located proximate to the ventilator.

In another aspect of the disclosure, a method of removing moisture and controlling condensation and humidity in a breathing circuit comprises providing a moisture removal and condensation and humidity management apparatus; receiving the flow of breathing gas from the patient into the breathing gas conduit of the breathing circuit tubing; receiving the flow of dry gas having into the dry gas conduit of the breathing circuit tubing for removing moisture from the breathing gas conduit; heating the at least one heated wire having a portion provided in the breathing gas conduit such that the flow of breathing gas at the downstream end of the breathing circuit tubing is heated to a higher temperature than the flow of breathing gas at the upstream end of the breathing circuit tubing thereby reducing or preventing condensation at the downstream end proximate to a ventilator; transferring moisture from the breathing gas conduit to the dry gas conduit through the moisture transmission pathway.

There has thus been outlined certain embodiments of the disclosure in order that the detailed description thereof herein may be better understood, and in order that the present contribution to the art may be better appreciated. There are additional embodiments of the disclosure that will be described below and which form the subject matter of the claims appended hereto.

In this respect, before explaining at least one embodiment of the disclosure in detail, it is to be understood that the disclosure is not limited in its application to the details of construction and to the arrangements of the components set forth in the following description or illustrated in the drawings. The disclosure is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present disclosure. It is important, therefore, that the

DETAILED DESCRIPTION

Figure 1:
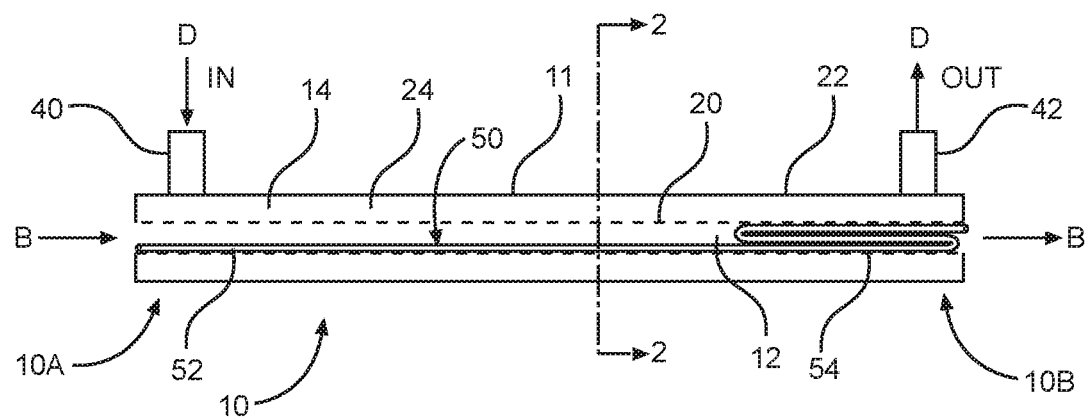
FIG. 1 is a schematic view illustrating an apparatus in accordance with one or more embodiments of the present disclosure incorporated into or as part of a breathing gas circuit.

The disclosure will now be described with reference to the drawing figures, in which like parts are referred to with like reference numerals throughout. One or more embodiments in accordance with the present disclosure provide a moisture removal and condensation and humidity management apparatus for a breathing circuit to rapidly remove water vapor or condensate from a humidified medical gas traveling through a breathing circuit between a ventilator and a patient or the patient and the ventilator. As used herein, a "breathing circuit" or "breathing gas circuit" is any arrangement of tubes or conduits which carries gases to be administered to and from a patient, such as from a ventilator, and which may include additional accessories or devices attached to it. Such "breathing gases" may include oxygen, air or any component thereof, and are configured to absorb high levels of moisture and/or to be humidified prior to administration to a patient, or during administration to a patient, suitable for medical applications.

FIG. 1 is a schematic view illustrating an apparatus incorporated into or as part of a breathing gas circuit in accordance with one or more implementations of the present disclosure. A moisture removal and condensation and humidity management apparatus 10 for a breathing circuit includes a section or length of breathing circuit tubing 11 defining a breathing gas conduit 12 for a flow (B) of breathing gas therein. The breathing gas flows from a first, upstream end 10A of the device 10, through the conduit 12 defined within device 10, to a second, downstream end 10B of the device 10. The breathing gas is configured to have a first humidity level and a level of moisture therein, which may be calibrated based on the needs of the patient. In one implementation, such a length of breathing circuit tubing 11 may be in an expiratory limb of a breathing circuit, such as, for example, between a patient and a ventilator.

In the device 10, a dry gas conduit 14 is defined adjacent at least a portion of the breathing gas conduit 12 between the first end 10A and second end 10B, for a dry gas flow (D) therein. The dry gas flow (D) is configured to have a second humidity level which is lower than the first humidity level within the breathing gas conduit (B). A dry gas flow is coupled from a dry gas source (not shown) to one or more input ports 40 which feed the dry gas flow (D) into the dry gas conduit 14, which then flows substantially parallel to, or around the breathing gas conduit 12. The dry gas conduit 14 further comprises one or more output ports 42 that may be in communication with an ambient environment surrounding the apparatus 10. A source of suction may be connected to the one or more output ports of the dry gas conduit. As shown in FIG. 1, the one or more output ports 42 may be located at the downstream end of the breathing circuit tubing 11. Further, each output or exit port 42 for the dry gas conduit may further include a filter, the dry gas exiting via the exit port to the ambient environment surrounding the apparatus. Such an exit port may also be connected to a source of suction. An input port 40 for the dry gas conduit may include a flow or volumetric control element for the dry gas flow.

The breathing circuit tubing 11 may comprise at least one heating element, such as a heated wire 50. The heated wire 50 has a length extending from an upstream end 10A of the breathing circuit tubing 11 to a downstream end 10B of the breathing circuit tubing 11. The heated wire 50 is configured to provide heat to the flow of breathing gas such that the breathing gas at the downstream end 10B of the breathing circuit tubing 11 is superheated, or heated to a higher temperature than the breathing gas at the upstream end 10A of the breathing circuit tubing 11. Thus, the heated wire 50 is configured to provide additional heating to the breathing gas at the downstream end 10B proximate to a ventilator in an expiratory limb of the breathing circuit so that excess condensation can be removed from the expiratory limb as well as from components, such as the ventilator, that receive the flow of breathing gas after passing through the expiratory limb. This configuration of the heating wire 50 reduces or eliminates excessive condensation prior to the gases entering the ventilator or respirator.

The heated wire 50 comprises an upstream portion 52 corresponding to the upstream end 10A of the breathing circuit tubing 11, and a downstream portion 54 corresponding to the downstream end 10B of the breathing circuit tubing 11. The heated wire 50 may be configured to have a variable thermal distribution profile in which the downstream end 10B of the breathing circuit tubing 11 is heated more than the upstream end 10A of the breathing circuit tubing 11. In some implementations, such a variable temperature distribution, in which the downstream portion 54 of the heated wire 50 is superheated relative to the upstream portion 52, may be achieved by folding the downstream portion 54 of the heated wire 50 back over itself. For instance, referring to FIG. 8A, the folded-over downstream portion 54 of the heated wire 50 may be generally S-shaped while the upstream portion 52 remains generally straight.

Figure 8A:
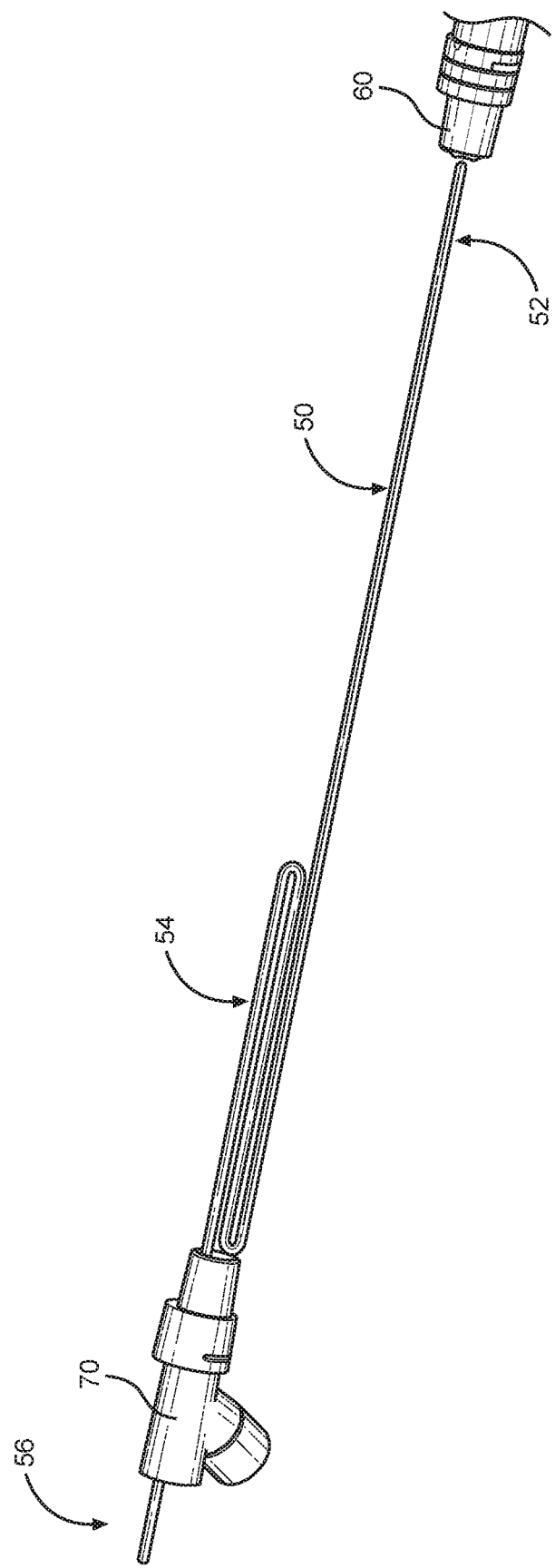
FIGS. 8A and 8B are perspective views of a heating element in accordance with one or more embodiments of the apparatus of the present disclosure.
Figure 8B:
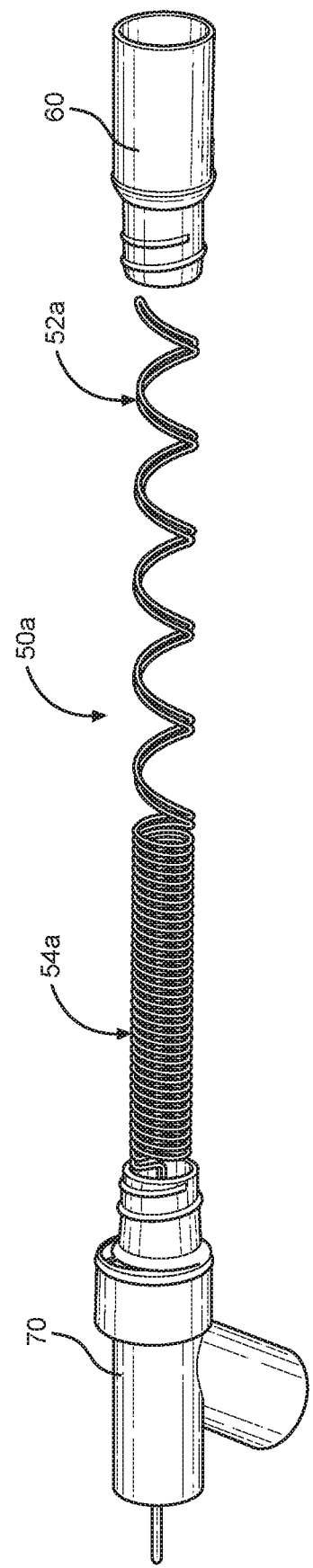

In other implementations, the heated wire 50 itself may have a variable resistance such that the downstream portion 54 of the wire can be heated more than the upstream portion 52 of the wire, thus resulting in a variable thermal distribution in which the downstream end 10B of the breathing circuit tubing 11 is correspondingly heated more than the upstream end 10A of the breathing circuit tubing 11. In still other implementations, the heating element may be a coiled heated wire 50a, as shown in FIG. 8B, wherein the pitch spacing between adjacent coils at the upstream portion 52a is different than the pitch spacing between adjacent coils at the downstream portion 54a. A variable thermal distribution of the coiled heated wire 50a may be achieved by spacing adjacent coils closer to each other at the downstream portion 54a and spacing adjacent coils farther from each other at the upstream portion 52a in order to superheat the downstream portion 54a of the heated wire 50a relative to the upstream portion 52a. A portion of the coiled heated wire 50a may be provided within a lumen of the tubing, or may be embedded within a wall of the tubing.

Referring again to FIG. 8A, the amount of folding of the downstream portion 54 of the heated wire 50 can be configured to provide a desired temperature increase near the ventilator end of the breathing circuit tubing 11 in an expiratory limb in order to superheat the breathing gas at the downstream end 10B in the breathing conduit 12 so as to reduce or prevent rain out near the inlet of the ventilator. The straight upstream portion 52 of the wire may be located within the breathing circuit tubing of the expiratory limb such that it does not enter a patient interface connector 60. Similarly, the folded downstream portion 54 of the wire 50 may be located within the breathing circuit tubing of the expiratory limb such that it does not enter a ventilator interface connector 70. An attachment end 56 of the heated wire 50 may be coupled to an electrical connector and/or a power source having electrical components that direct power through the heater wire 50 in order to heat it. The attachment end 56 may extend through the ventilator interface connector 70 from the folded downstream portion 54, as shown in FIG. 8A.

Superheating the breathing gas at the downstream end 10B of the breathing circuit tubing 11 insures that the breathing gas exits the circuit 11 at a temperature much farther away from the dewpoint than the temperature of the breathing gas at the upstream end 10A of the tubing 11. Thus, the heated wire 50 is able to prevent or reduce moisture accumulation in expiratory filters, expiratory cartridges, expiratory flow sensors, or any other components located downstream from the expiratory limb. Further, such a variable temperature profile of the heated wire 50 assists in managing the amount of moisture that occurs within the expiratory limb itself by cooling the breathing gas in the upstream end 10A of the tubing 11 and thus forcing more condensate removal from the circuit 11.

Figure 2:
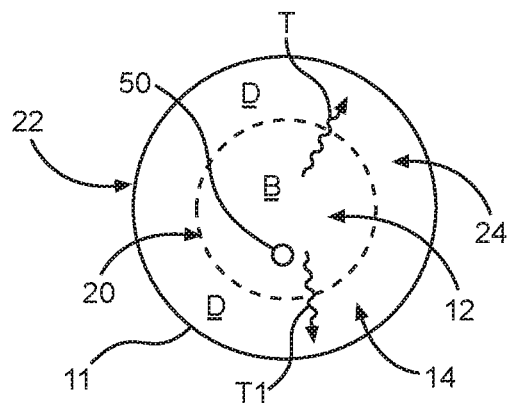
FIG. 2 is a schematic cross-sectional view illustrating the apparatus of FIG. 1 along line 2-2.

Turning to FIG. 2, a schematic cross-sectional view illustrating the apparatus of FIG. 1 is shown. As shown in FIG. 2, the dry gas conduit 14 may be an annular flow space which is concentric with breathing gas conduit 12. The breathing circuit tubing 11 may be formed by an inner tube 20 defining the breathing gas conduit 12, and the dry gas conduit 14 is formed by an outer sleeve or tube 22 surrounding the inner tube 20, the dry gas conduit 14 thereby being defined as an annular flow conduit 24 defined between the inner tube 20 and outer tube 22. One, or both, of the inner tube 20 and the outer tube 22 may be corrugated. Alternatively, the inner tube 20 could define the dry gas conduit 14 and the annular space 24 between the inner and outer tubes 20, 22 could be the breathing gas conduit 12. In the present disclosure, a sufficient stretch of surface area is shared along the breathing circuit tubing 11 between the breathing gas conduit 12 and dry gas conduit 14 such that a moisture and humidity transmission pathway is enabled between the two conduits, as further described below. A portion of the heated wire 50 may be provided within the breathing gas conduit 12. In some implementations, a portion of the heated wire 50 may be provided within a lumen of the inner tube 20. In other implementations, a portion of the heated wire 50 may be embedded within a wall of the inner tube 20.

The apparatus 10 further comprises a moisture transmission pathway between the breathing gas conduit 12 and the dry gas conduit 14, such that humidity in the flow of breathing gas (B) is lowered and moisture in the flow of breathing gas (B) is transferred to the dry gas flow (D). As shown in FIG. 2, such a moisture transmission pathway (T) occurs between the higher humidity breathing gases in conduit 12 and the lower humidity dry gas flow in conduit 14. A user can increase or decrease the level of dry gas supplied to the circuit to manage or remove the condensate which may be transmitted from the breathing gas (B) to the dry gas conduit. The moisture level thus may be reduced from within the breathing gas flow and transferred to the dry gas flow. The breathing circuit tubing 11 may comprise a permeable portion along part or all of the inner conduit 20, which is permeable to water vapor but impermeable to liquid water, such that the moisture transmission pathway (T) is provided by such permeable portion of the breathing circuit tubing. The materials comprising the permeable portion are water vapor breathable and allow passage of water vapor.

The permeable portion may form some or all of the walls of the breathing gas conduit 12, such as inner tube 20, and may include a single, or composite outer, layer of water vapor breathable medium. In one implementation, an additional wicking layer may be added to the permeable portion. Such a wicking layer may be disposed as an inner layer of inner conduit 20 and configured to be in contact with breathing gas flow (B) inside said conduit. Such a wicking layer may be made of wicking material which allows for adsorption and/or absorption of both moisture and water in any phase, gas or liquid, using a capillary action, while the outer layer of water vapor breathable medium permits the passage of water vapor only and not liquid water.

Examples of wicking material in the inner layer are a knit or non-woven cloth or fabric, and can be synthetic and made of polyester, polyester and polypropylene blends, nylon, polyethylene or paper, and can be microfilaments or microfiber material such as Evolon® brand fabric material made by Freudenberg & Co. KG. A particular example of wicking material would be a non-woven material of 70% polypropylene and 30% polyester. Another example of the wicking material can be Evolon® brand fabric material having a weight of 60 or 80 grams per square meter. Examples of the outer layer of water vapor breathable medium are Sympatex® brand water vapor permeable membranes made of polymers made by Sympatex Technologies, including monolithic hydrophilic polyester ester membrane, including, as one example, a 12 micron thick membrane.

In another implementation of the present disclosure, the breathing circuit tubing 11 may comprise one or more small openings or perforations in inner tube 20 which permit drainage of liquid water from the breathing gas conduit 12 to the dry gas conduit 14, such that another, different, moisture transmission pathway T1 is provided by such one or more perforations between the breathing gas flow (B) and dry gas flow (D), as shown in FIG. 2.

Figure 3:
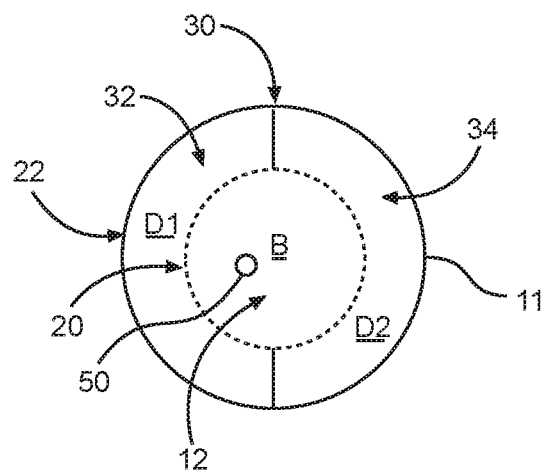
FIG. 3 is a schematic cross-sectional view illustrating the apparatus of FIG. 1 in one or more additional embodiments of the present disclosure.

FIG. 3 is a schematic cross-sectional view illustrating the apparatus of FIG. 1 according to one or more additional embodiments of the present disclosure. In FIG. 3, a dividing wall 30 is formed between the inner tube 20 and outer tube 22 in the annular space between said tubes to divide the dry gas conduit into a first, delivery conduit 32 for flow of dry gas (D1) from a first end of the apparatus 10 to a second end of the apparatus, and a second, return conduit 34 for flow of dry gas (D2) from the second end of the apparatus to the first end of the apparatus 10. In this way, the dry gas flow may be re-used, such as, for example, in a closed loop system. A portion of the heated wire 50 may be provided within the breathing gas conduit 12, and more particularly, may be provided within a lumen of the inner tube 20. In another implementation, a portion of the heated wire may be embedded within a wall of the inner tube 20. One or more moisture transmission pathways may be defined between breathing gas flow conduit (B) and one or both of dry gas conduits (D1, D2), including a permeable membrane incorporated into inner tube 20 as described herein, or a series of perforations in the inner tube 20, as also described herein. The permeable membrane is permeable to water vapor but impermeable to liquid water and may include one or more layers, including a wicking layer, as described above.

Figure 4:
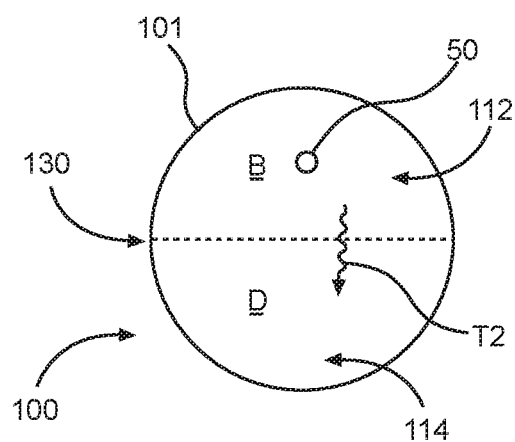
FIG. 4 is a schematic cross-sectional view illustrating the apparatus of FIG. 1 in one or more additional embodiments of the present disclosure.

FIG. 4 is a schematic cross-sectional view of an apparatus 100 incorporated into or as part of a breathing gas circuit in accordance with one or more additional embodiments of the present disclosure. In FIG. 4, a breathing circuit tubing 101 defines a breathing gas conduit 112 for a flow of breathing gas flow (B) therein, said breathing gas having a first humidity level and a level of moisture therein, and a dry gas conduit 114 is formed adjacent at least a portion of the breathing gas conduit 112 for a dry gas flow (D) therein, said dry gas flow configured to have a second humidity level lower than the first humidity level. In FIG. 4, a moisture transmission pathway (T2) is provided between the breathing gas conduit 112 and the dry gas conduit 114, such that humidity in the flow of breathing gas (B) is lowered and moisture in the flow of breathing gas (B) is transferred to the dry gas flow (D). In FIG. 4, the breathing gas conduit 112 and dry gas conduit 114 share a common dividing wall 130, the common dividing wall 130 having the moisture transmission pathway (T2), which may be provided by a permeable membrane incorporated into part or all of the dividing wall 130, as described herein, or a series of perforations in part or all of the dividing wall 130, as also described herein. The permeable membrane is permeable to water vapor but impermeable to liquid water and may include one or more layers, including a wicking layer, as described above. A portion of the heated wire 50 may be provided within the breathing gas conduit 112.

Figure 5:
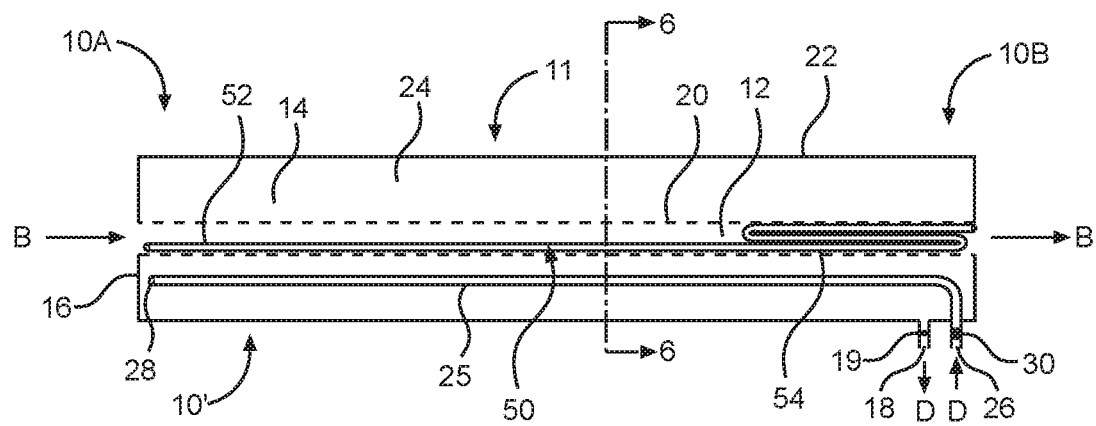
FIG. 5 is a schematic view illustrating an apparatus in accordance with one or more embodiments of the present disclosure that may be incorporated into or as part of a breathing gas circuit.

FIG. 5 is a schematic view illustrating another implementation of the moisture removal and condensation and humidity management apparatus 10' for a breathing circuit according to the present disclosure. The dry gas conduit 14 may include a closed end 16 on the upstream end 10A, and an outlet 18 at the downstream end 10B. The outlet 18 may be in communication with a source of suction and/or the ambient environment around the apparatus 10. In some embodiments, the outlet 18 may be in communication with a filter 19.

The apparatus 10' may include a feeding conduit 25 configured to supply dry gas to the dry gas conduit 14. As depicted in FIG. 5, the feeding conduit 25 may include an inlet 26 at the downstream end 10B of the apparatus 10, and an outlet 28 at the first end 10B of the apparatus 10', such that the feeding conduit 25 extends through at least a portion of the dry gas conduit 14. For example, the feeding conduit 25 may extend greater than half of the length of the dry gas conduit 14. In some embodiments, the feeding conduit 25 may extend substantially the entire length of the dry gas conduit 14. Advantageously, the feeding conduit 25 may allow the inlet 26 and outlet 18 for dry gas of the apparatus 10' to be further away from the patient, reducing any potential safety risk to the patient. This prevents any potential sparking caused by the ingress and egress of the dry gas proximate the patient. Furthermore, by providing the outlet 18 of the feeding conduit 25 at the upstream end 10A within the dry gas conduit 14, the apparatus 10' may provide a large surface area for moisture/humidity transfer from the breathing gas conduit 12 to the dry gas conduit 14. In some embodiments, a flow or volume control element 30, such as a valve, may be connected to the inlet 26 of the feeding conduit 25 and configured to control the flow of dry gas into the feeding conduit 25.

The breathing circuit tubing 11 of the apparatus 10' may further comprise at least one heating element, such as a heated wire 50 as previously described. The heated wire 50 has a length extending from an upstream end 10A of the breathing circuit tubing 11 to a downstream end 10B of the breathing circuit tubing 11. The heated wire 50 is configured to provide heat to the flow of breathing gas such that the breathing gas at the downstream end 10B of the breathing circuit tubing 11 is superheated, or heated to a higher temperature than the breathing gas at the upstream end 10A of the breathing circuit tubing 11. The heated wire 50 comprises an upstream portion 52 corresponding to the upstream end 10A of the breathing circuit tubing 11, and a downstream portion 54 corresponding to the downstream end 10B of the breathing circuit tubing 11. The heated wire 50 is configured to have a variable thermal distribution profile in which the downstream end 10B of the breathing circuit tubing 11 is heated more than the upstream end 10A of the breathing circuit tubing 11 by folding the downstream portion 54 of the heated wire 50 back over itself.

Figure 6:
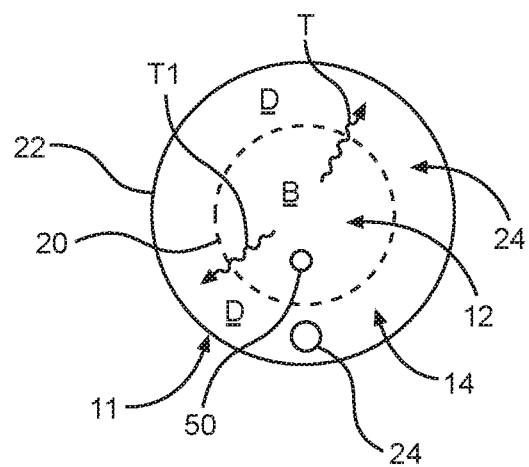
FIG. 6 is a schematic cross-sectional view illustrating the apparatus of FIG. 5 along line 6-6.

FIG. 6 is a schematic cross-sectional view illustrating the apparatus 10' of FIG. 5. The dry gas conduit 14 may be an annular flow space which is concentric with breathing gas conduit 12. For example, the breathing circuit tubing 11 may include an inner tube 20 defining the breathing gas conduit 12, and an outer sleeve or tube 22 surrounding the inner tube 20 and defining the dry gas conduit 14. The dry gas conduit 14 thereby may include an annular conduit 24 defined between the inner tube 20 and outer tube 22. Alternatively, in some embodiments, the inner tube 20 may define the dry gas conduit 14 and the annular conduit 24 between the inner tube 20 and the outer tube 22 may include the breathing gas conduit 12. As depicted, the feeding conduit 25 may extend through the dry gas conduit 14. Further, a portion of the heated wire 50 may be provided within the breathing gas conduit 12. In some implementations, a portion of the heated wire 50 may be provided within a lumen of the inner tube 20. In other implementations, a portion of the heated wire 50 may be embedded within a wall of the inner tube 20. One or both, of the inner tube 20 and the outer tube 22 may be corrugated. In the present disclosure, a moisture transmission pathway may be positioned between the breathing gas conduit 12 and the dry gas conduit 14. For example, a sufficient stretch of surface area of the breathing circuit tubing 11 may be shared between the breathing gas conduit 12 and the dry gas conduit 14 enabling transfer of moisture between the flow of breathing gas (B) and the flow of dry gas (D), as further described below.

The present disclosure provides one or more embodiments which provide the moisture transmission pathway between the breathing gas conduit 12 and the dry gas conduit 14, lowering the moisture and/or humidity in the flow of breathing gas (B) by transferring the moisture and/or humidity to the dry gas flow (D). For example, in FIG. 6, the moisture transmission pathway (T) may occur between the higher humidity breathing gases in breathing gas conduit 12 and the lower humidity dry gas flow in dry gas conduit 14. A user may increase or decrease the level of dry gas supplied to the dry gas conduit 14 to manage or remove the condensate which may be transferred from the breathing gas (B) to the dry gas (D). The moisture level thus may be reduced from within the breathing gas flow (B) and transferred to the dry gas flow (D).

As further shown in FIG. 6, the breathing circuit tubing 11 may include a permeable portion or membrane (as depicted in broken lines) along part or all of the inner tube 32. The permeable portion may be permeable to water vapor but impermeable to liquid water, such that the moisture transmission pathway (T) is provided by the permeable portion of the breathing circuit tubing 11. The permeable portion may include one or more materials that are water vapor breathable and allow passage of water vapor, as is well known to those of ordinary skill in the art. The permeable portion may form some or all of the walls of the breathing gas conduit 12 (e.g., inner tube 20) and may include a single, or composite layer of water vapor breathable medium. For example, in some embodiments, the permeable portion may include an inner layer and an outer layer having different permeability/wicking properties. A first wicking layer may be provided as an inner layer of inner tube 20 and may be configured to contact the breathing gas flow (B) inside of the inner tube 20. The wicking layer may be made of one or more wicking materials that allow for adsorption and/or absorption of moisture and/or water in any phase (e.g., gas and/or liquid), for example, through capillary action. The permeable portion may also include an outer layer of water vapor breathable material that permits the passage of water vapor only, while not permitting passage of liquid water.

In some embodiments, the breathing circuit tubing 11 may, additionally or alternatively, include one or more small openings or perforations in the inner tube 20 which permit drainage of liquid water from the breathing gas conduit 12 to the dry gas conduit 14. Therefore, a second moisture transmission pathway T1 may be provided by the one or more perforations between the breathing gas flow (B) and dry gas flow (D), as shown in FIG. 6. Although, the transmission pathway (T) and the second transmission pathway (T1) are depicted in the same cross-sectional view of FIG. 6, the transmission pathways (T, T1) may be provided in the alternative and/or at different portions along the breathing circuit tubing 11. The transmission pathway (T) and the second transmission pathway (T1) may be provided in a gradient along the length of the inner tube 20. For example, in some embodiments, the inner tube 20 may have more permeability at the upstream end 10A than the downstream end 10B, increasing moisture transfer when the breathing gas enters the breathing gas conduit 12 reducing condensation in remaining length of the inner tube 20. In some embodiments, the inner tube 20 may have more permeability on the downstream end 10B than the upstream end 10A, increasing moisture transfer when the moisture of the breathing gas is lower.

Figure 7:
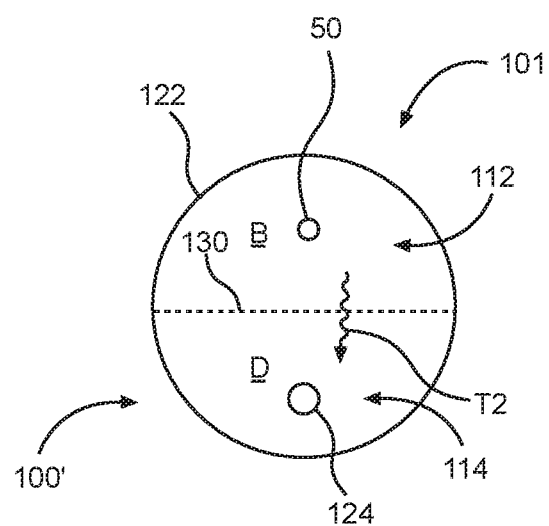
FIG. 7 is a schematic cross-sectional view illustrating the apparatus of FIG. 5 in one or more additional embodiments of the present disclosure.

FIG. 7 is a schematic cross-sectional view of an apparatus 100' incorporated into or as part of a breathing gas circuit in accordance with one or more additional embodiments of the present disclosure and depicting a breathing circuit tubing 101 having a tube 122 including a breathing gas conduit 112 configured to receive a flow of breathing gas flow (B). The breathing gas may have a first humidity level and a first level of moisture. The tube 122 may also include a dry gas conduit 114 configured to receive a dry gas flow (D). The dry gas flow may have a second humidity level lower than the first humidity level, and/or a second level of moisture lower than the first level of moisture. The dry gas conduit 114 may be adjacent to at least a portion of the breathing gas conduit 112. A feeding conduit 124 may extend through the dry gas conduit 114. A portion of the heated wire 50 may extend through the breathing gas conduit 112.

As further depicted in FIG. 7, a moisture transmission pathway (T2) may be provided between the breathing gas conduit 112 and the dry gas conduit 114, such that moisture and/or humidity may be transferred from the breathing gas (B) to the dry gas flow (D) based on the differential humidity/moisture levels. Further, the breathing gas conduit 112 and dry gas conduit 114 may share a common dividing wall 130 providing the moisture transmission pathway (T2). For example, the moisture transmission pathway (T2) may be provided by a permeable portion or membrane (depicted as broken lines) incorporated into part or all of the dividing wall 130, as described herein, or a series of perforations in part or all of the dividing wall 130, as also described herein. The permeable portion may be permeable to water vapor but impermeable to liquid water and may include one or more layers, including a wicking layer, as described above.

In one or more embodiments of the present disclosure, the dry gas conduit 14, 114 may be closed to ambient air around the apparatus. The dry gas conduit 14, 114 therefore can be configured to provide a stream of dry gas flow at humidity levels which are significantly lower than the humidity in the breathing gas conduit 12, 112. In some embodiments, the apparatus 10 may include one or more sensors configured to detect the first humidity level of the breathing gas conduit 12 and the second humidity level of the dry gas conduit 14.

Figure 9:
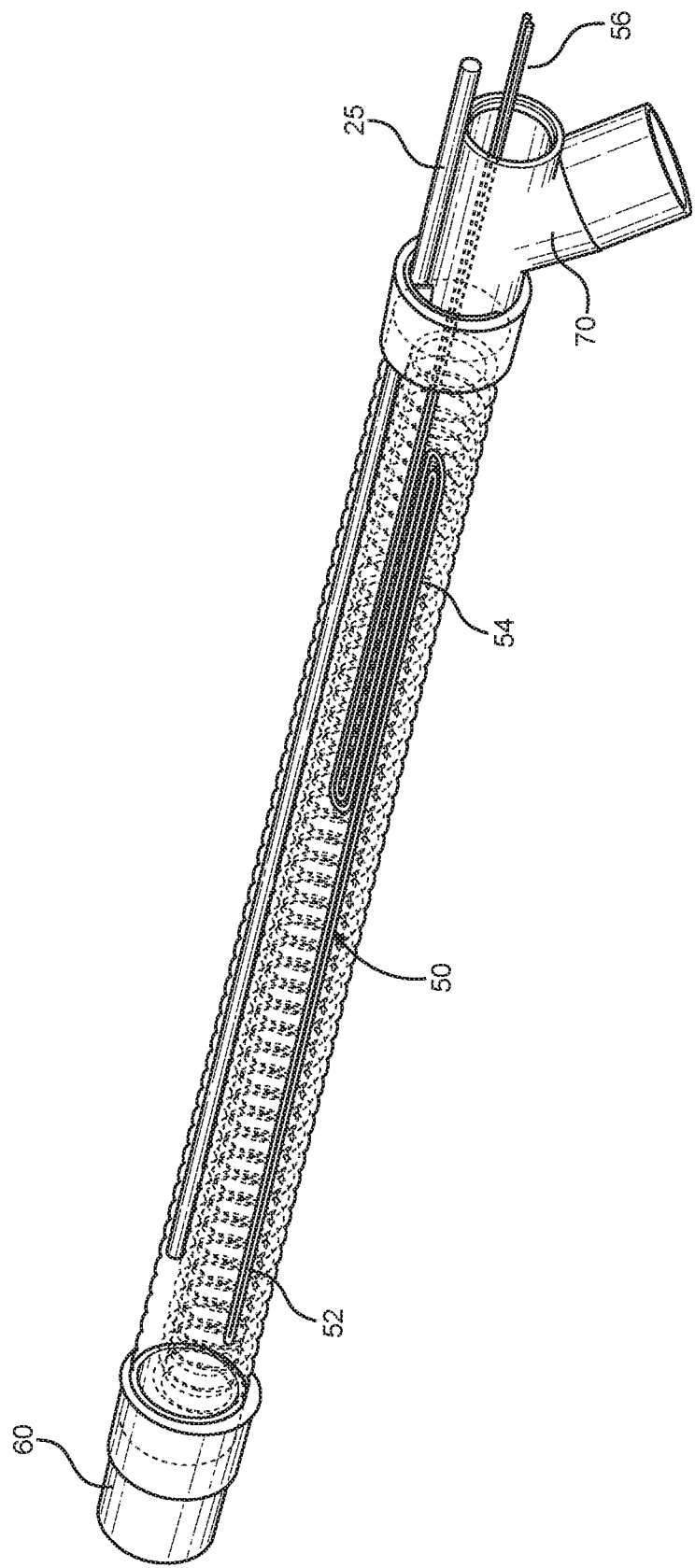
FIG. 9 is a perspective view of a limb of a breathing circuit including a heating element in accordance with one or more additional embodiments of the present disclosure.
Figure 10:
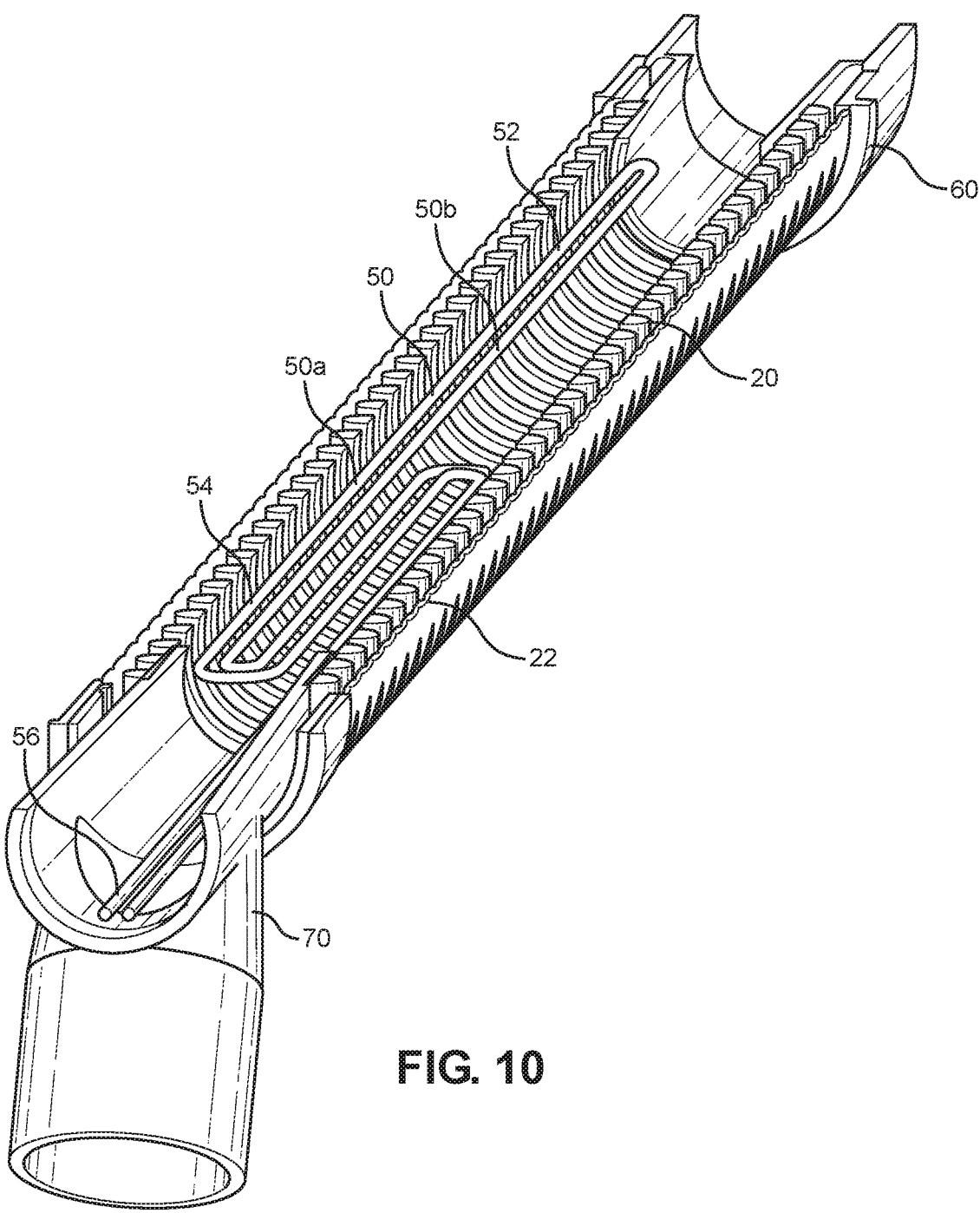
FIG. 10 is a top perspective cross-sectional view of the breathing circuit limb and heating element of FIG. 9.
Figure 11:
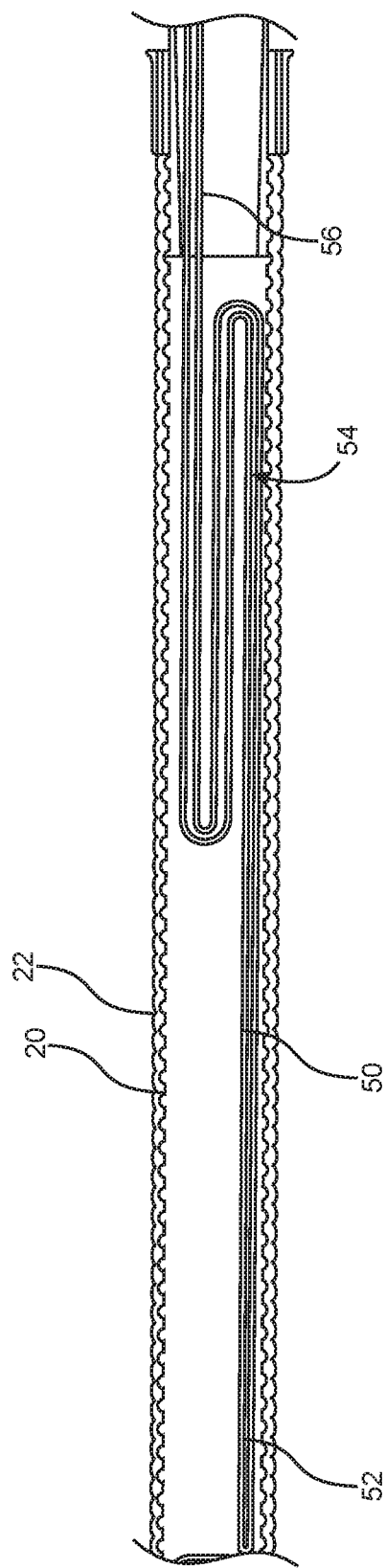
FIG. 11 is a top cross-sectional view of the breathing circuit limb and heating element of FIG. 9.

Referring to FIGS. 9-11, the heated wire 50 may comprise two wire strand portions 50A, 50B that are connected to each other at the upstream portion 52 of the heated wire. The downstream portion 54 of the heated wire 50 may be folded back upon itself such that six wire strand portions are formed at the downstream end 54 for superheating the breathing gas. Breathing gas heated by the downstream portion 54 of the heated wire 50 has a lower absolute humidity and a higher temperature than breathing gas heated by the upstream portion 52 of the wire 50.

Heating the breathing gas to a greater temperature at the downstream end of an expiratory limb increases the temperature differential between the dew point temperature and the actual air temperature. Breathing gas that exits the breathing circuit cool in components such as unheated expiratory filters that are exposed to ambient air conditions, and thus raising the temperature at the downstream end allows for the breathing gas to cool and prevents water vapor from condensing on cool surfaces. Thus, less heating of the breathing gas at the upstream end 10A of the expiratory limb results in a cooler temperature at that point in the breathing circuit, which correspondingly allows for more condensation that permeates through the wall of the circuit, thus reducing the absolute humidity of the breathing gas as will be described in detail below.

The present disclosure therefore uses the differential between humidity or moisture content between the respective flows in the breathing gas conduit 12, 112, compared to the dry gas conduit 14, 114, which allows for greater extraction or diffusion of moisture and humidity from the breathing gas flow to the dry gas flow, which is further assisted by the convective action of the dry gas flow along the common surface area shared between the breathing gas conduit 12, 112, and the dry gas conduit 14, 114, such as along inner tube 20, or common dividing wall 130.

Figure 12:
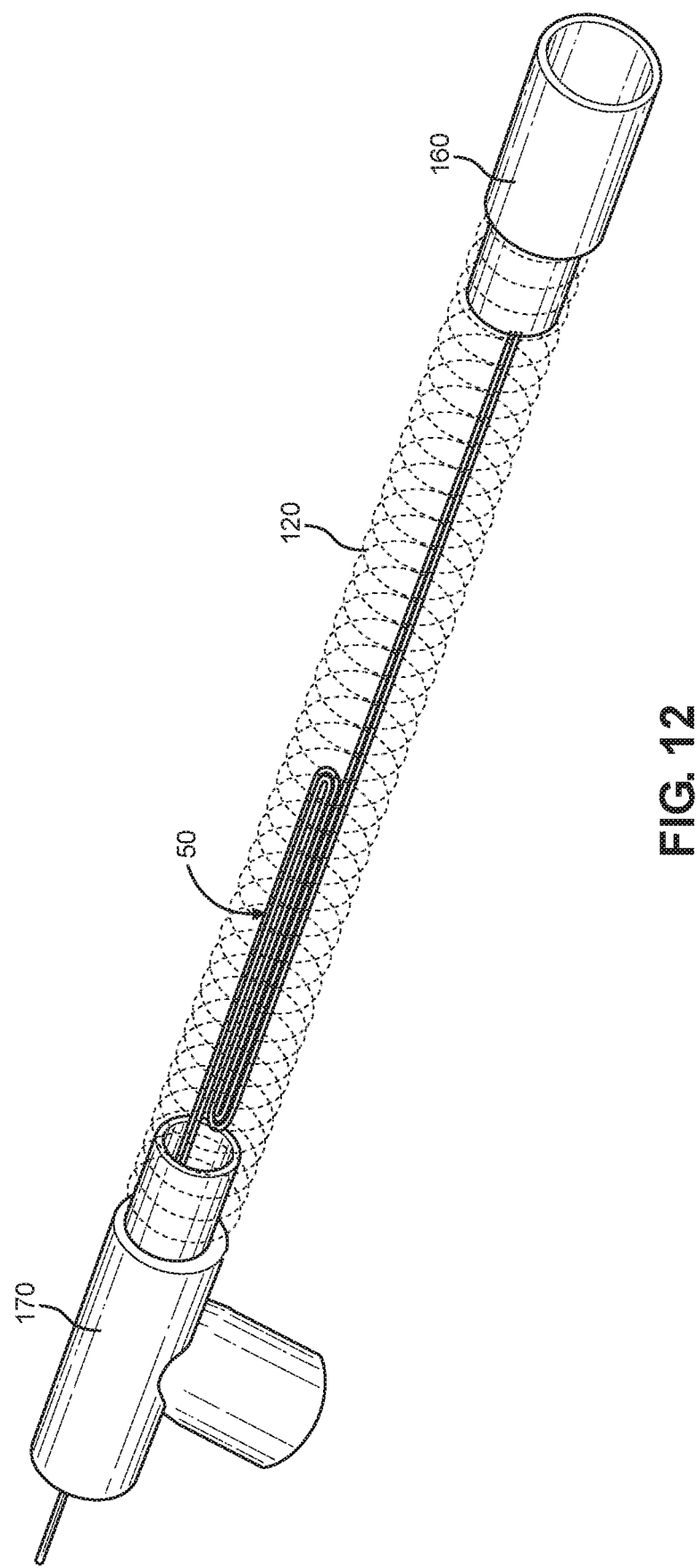
FIG. 12 is a perspective view of a limb of a breathing circuit including a heating element in accordance with one or more additional embodiments of the present disclosure.

Referring to FIG. 12, another implementation of a moisture removal and condensation and humidity management apparatus for a breathing circuit arranged between a patient and a ventilator is shown. This apparatus comprises breathing circuit tube 120 that defines a breathing gas conduit configured to receive a flow of breathing gas. A patient interface connector 160 is connected to one end of the tube 120, and a ventilator interface connector 170 is connected to an opposite end of the tube. The tube may comprise a moisture transmission pathway configured to enable transfer of moisture from the breathing gas conduit directly to ambient air. A heating element, such as at least one heated wire 50 having a length extending from an upstream end of the breathing circuit tubing 120 to a downstream end of the breathing circuit tubing 120, may be provided within the lumen of the tube 120 or may be embedded within a wall of the tube 120. Various types of heated wires and heated wire configurations, as previously described, above may be used. The at least one heated wire 50 is configured to provide heat to the flow of breathing gas such that the breathing gas at the downstream end is heated to a higher temperature than the breathing gas at the upstream end. The moisture transmission pathway comprises a permeable membrane that is permeable to water vapor but impermeable to liquid water. Further, the permeable membrane forms a portion of said breathing circuit tubing 120. The breathing circuit tubing 120 may be an expiratory limb of the breathing circuit such that the upstream end of the breathing circuit tubing is located proximate to a patient and the downstream end of the breathing circuit tubing is located proximate to the ventilator.

The present disclosure therefore provides a superior way of removing moisture or water vapor from a breathing circuit, which is better than water traps or other fluid dissipation or moisture removal devices known in the prior art. The result of the inventive apparatus disclosed is that when the apparatus is coupled with a breathing circuit, rainout or condensation in the breathing tube and collection of water within the breathing circuit is significantly reduced. The present disclosure therefore allows for removal of the collected condensate on the inner walls of a breathing gas conduit, which may then be transported away through an outer sleeve or tube which provides the dry gas conduit. The heated wire of the apparatus assists with removal of excess condensation from an expiratory limb and from collecting on components that receive the breathing gas flow, such as a ventilator and an expiratory filter, after exiting the expiratory limb.

The outer tube of the apparatus can also protect the inner tube from damage or puncture, which can be especially vulnerable to damage or puncture when it incorporates a permeable membrane and/or perforations as described herein. To provide additional strength and puncture protection, an additional outer cover structure can be added to the apparatus. The present disclosure therefore represents an improvement over the known prior art by providing the benefits of: (a) reducing or eliminating user management of condensate levels within a breathing circuit, and/or (b) reducing the humidity output from an expiratory limb of a breathing circuit to reduce the collection of condensate which may be collected in the ventilator.

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

What is claimed is:

1. A moisture removal and condensation and humidity management apparatus for a breathing circuit arranged between a patient and a ventilator, the apparatus comprising:
   a breathing circuit tubing defining a breathing gas conduit and a dry gas conduit adjacent at least a portion of the breathing gas conduit, the breathing gas conduit configured to receive a flow of breathing gas having a first humidity level and the dry gas conduit configured to receive a flow of dry gas having a second humidity level lower than the first humidity level;
   at least one heated wire having a length extending from an upstream end of the breathing circuit tubing to a downstream end of the breathing circuit tubing, the at least one heated wire configured to provide heat to the flow of breathing gas such that the breathing gas at the downstream end is heated to a higher temperature than the breathing gas at the upstream end;
   a moisture transmission pathway between the breathing gas conduit and the dry gas conduit and configured to enable transfer of moisture from the breathing gas to the dry gas based on a humidity differential between the first and second humidity levels,
   further comprising a feeding conduit extending through at least a portion of the dry gas conduit, the feeding conduit configured to supply the dry gas into the dry gas conduit.

2. The apparatus of claim 1, wherein the moisture transmission pathway comprises a permeable membrane that is permeable to water vapor but impermeable to liquid water.

3. The apparatus of claim 2, wherein the permeable membrane forms a portion of said breathing circuit tubing.

4. The apparatus of claim 1, wherein a portion of the at least one heated wire is provided within the breathing gas conduit.

5. The apparatus of claim 1, wherein the at least one heated wire comprises two wire strand portions connected to each other at the upstream end of the breathing circuit tubing proximate the patient.

6. The apparatus of claim 1, wherein a portion of the at least one heated wire is folded back upon itself at the downstream end proximate the ventilator.

7. The apparatus of claim 6, wherein the portion of the at least one heated wire folded back upon itself is generally S-shaped.

8. The apparatus of claim 1, wherein a portion of the at least one heated wire is folded over itself at the downstream end of the breathing circuit tubing proximate the ventilator such that six wire strand portions are formed at the downstream end.

9. The apparatus of claim 1, wherein the at least one heated wire comprises a variable resistance such that a downstream portion of the at least one heated wire can be heated more than an upstream portion of the at least one heated wire.

10. The apparatus of claim 1, wherein the at least one heated wire comprises coils having a pitch spacing between adjacent coils at an upstream portion of the at least one heated wire that are different than a pitch spacing between adjacent coils at a downstream portion of the at least one heated wire.

11. The apparatus of claim 1, wherein the breathing circuit tubing is formed by an inner tube defining the breathing gas conduit, and the dry gas conduit is formed by an outer tube surrounding the inner tube, the dry gas conduit being defined by an annular flow conduit defined between the inner tube and the outer tube.

12. The apparatus of claim 11, further comprising a dividing wall formed between the inner tube and the outer tube in the annular flow conduit to divide the dry gas conduit into a delivery conduit for flow of dry gas from a first end of the breathing circuit tubing to a second end of the breathing circuit tubing, and a return conduit for flow of dry gas from the second end of the breathing circuit tubing to the first end of the breathing circuit tubing.

13. The apparatus of claim 11, wherein a portion of the heated wire is provided within a lumen of the inner tube.

14. The apparatus of claim 11, wherein a portion of the heated wire is embedded within a wall of the inner tube.

15. The apparatus of claim 1, wherein the breathing circuit tubing is an expiratory limb of the breathing circuit such that the upstream end of the breathing circuit tubing is located proximate to a patient and the downstream end of the breathing circuit tubing is located proximate to the ventilator.

16. The apparatus of claim 1, wherein the feeding conduit includes an inlet at the downstream end of the breathing circuit tubing.

17. The apparatus of claim 16, further comprising a flow control element connected to the inlet of the feeding conduit and configured to control the flow of the dry gas into the feeding conduit.

18. The apparatus of claim 1, wherein the feeding conduit includes an outlet at the upstream end of the breathing circuit tubing.

19. A method of removing moisture and controlling condensation and humidity in a breathing circuit, the method comprising:
    providing an apparatus as claimed in claim 1;
    receiving the flow of breathing gas from the patient into the breathing gas conduit of the breathing circuit tubing;
    receiving the flow of dry gas into the dry gas conduit of the breathing circuit tubing for removing moisture from the breathing gas conduit;
    heating the at least one heated wire having a portion provided in the breathing gas conduit such that the flow of breathing gas at the downstream end of the breathing circuit tubing is heated to a higher temperature than the flow of breathing gas at the upstream end of the breathing circuit tubing thereby reducing or preventing condensation at the downstream end proximate to the ventilator;
    transferring moisture from the breathing gas conduit to the dry gas conduit through the moisture transmission pathway.

* * * * *